United States Patent [19]

Cunningham

[11] 4,013,073
[45] Mar. 22, 1977

[54] DISPENSING DEVICE

[76] Inventor: James Robert Cunningham, 2010 Virginia Lane, Philadelphia, Pa. 19401

[22] Filed: May 14, 1975

[21] Appl. No.: 577,322

[52] U.S. Cl. .................................................. 128/216
[51] Int. Cl.² .................................................. A61M 5/00
[58] Field of Search ............ 128/216, 215, 218, 221, 128/231, 232, 239, 272; 222/107, 106, 211, 213, 214, 215

[56] References Cited
UNITED STATES PATENTS

| | | | |
|---|---|---|---|
| 1,336,730 | 4/1920 | Court | 128/216 |
| 2,676,591 | 4/1954 | Fox | 128/216 |
| 2,680,440 | 6/1954 | Fox | 128/216 |
| 2,688,964 | 9/1954 | Smith | 128/216 |
| 2,693,183 | 11/1954 | Lockhart | 128/216 |
| 3,192,925 | 7/1965 | Cunningham | 128/216 |
| 3,260,412 | 7/1966 | Larkin | 222/107 |
| 3,662,928 | 5/1972 | Pogorski et al. | 222/211 |
| 3,736,933 | 6/1973 | Szabo | 128/216 |

*Primary Examiner*—John D. Yasko
*Attorney, Agent, or Firm*—Paul & Paul

[57] ABSTRACT

A dispensing device of the syringe type is provided, that is constructed at its dispensing end for facilitating substantially complete discharge therefrom. Also, interior walls of the container are provided with mutual interconnecting means, and with the container being substantially flexible, the walls are secured together as they are pressed together, also for facilitating substantially complete discharge from the container. The device is particularly adapted for use with syringes of the throw-away type, for dispensing medicine, inoculation, or the like by means of a needle.

2 Claims, 7 Drawing Figures

DISPENSING DEVICE

BACKGROUND OF THE INVENTION

In the art directed to the disposable syringes, it is known to provide a collapsible container for expressing medicines and the like through a needle, into humans or animals, for example. In my earlier U.S. Pat. No. 3,192,925, a previous development of mine sets forth many of the parameters and utilities for devices of this type. However, in some instances it is desired to be able to express a predetermined quantity of medicine, inoculant or the like with precise measurement that can only obtained by discharging all of the medicine, serum, or other liquid from the flexible container.

In the device of my above-mentioned previous invention, at the discharge end of the tubular container, as the container is being flattened or squeezed into a flattened condition such as will facilitate the discharge, that portion of the container that is immediately adjacent the needle holder or needle carrier, but still inside the container, may not be flattened by compressing the opposite sidewalls of the tubular container together, due to the presence of the needle carrier. Thus, a zone of triangular cross-section often remains in the usual embodiment of my previous invention, whereby not quite all of the substance in the container is discharged therefrom. The problem in complete discharge of fluid from a container is similar to that that is experienced in attempting to discharge the last possible amount of toothpaste from a conventional toothpaste tube, such that the neck of the toothpaste tube, being generally non-flexible relative to the body of the tube, prohibits the complete discharge.

Also, in other syringe types of devices, it is not readily apparent when complete discharge from a flexible tube or container has been effected. The physician, nurse, or the like must be extremely careful to flatten the container completely, or a given injection may introduce an expression of less than the full or complete quantity of liquid in the container. In some instances, this can be highly critical, for example, in injecting insulin into the body of a diabetic, wherein a precise amount of insulin must be carefully controlled. If a given injection is "short" relative to the desired injection, serious consequences can result.

THE PRESENT INVENTION

The present invention is therefore principally addressed to providing a dispensing container of the syringe type that allows complete expression of a medicant or other liquid therefrom, and that effects such expression completely and as uniformly as possible, without variation in amount from occasion to occasion.

To this end, a particularly unique construction is provided for the end of the syringe adjacent the needle, to insure the facility for complete discharge, but yet allowing for the necessary and desired germ-free seal prior to penetration of the needle into the container. Also, an internal interlock is provided for opposite sides of the flattened container walls, such that, as the container is flattened, the opposite walls engage with each other, to assure to the person doing the dispensing that, upon interlocking, the expression or discharge has been complete up to that point. As the walls are further squeezed together by moving generally one's thumb and forefinger toward the discharge end of the syringe, along the tube, the complete expression across the tube is then completed throughout the entire length of the tube.

Thus, the present invention affords a device for carefully controlling the amount of and the completion of discharge of a medicant or the like from a syringe.

In its broader aspects, the present invention affords a capability of complete discharge of a liquid from any type of tube, by virtue of the interlocking walls of the tube, and additionally or independently, as desired, affords the capability of complete discharge even at that end of the tube or similar container that is next adjacent the exit opening or passageway, to overcome previous inabilities at discharging the usual residual amounts of liquid or the like. Also, in its broader applications, the present invention may also be usable with more viscous fluids, providing for the ease of and completion of discharge of such fluids from their containers.

Accordingly, it is a primary object of this invention to provide a novel syringe preferably of the disposable type.

It is a further object of this invention to provide a syringe capable of complete expression of a medicine that is contained therein, from the container portion thereof.

It is a further object of this invention to provide a syringe that enables the user to readily ascertain that complete expression has been obtained, by whether or not opposed wall portions of a flattened container are in contact with each other and preferably are in complete mutual interengagement with each other.

It is another object of this invention to provide a novel device for facilitating the dispensing of substances therefrom.

Other objects and advantages of the present invention will be readily apparent to those skilled in the art by reading of the following brief descriptions of the drawing figures, detailed descriptions of the preferred embodiments, and the appended claims.

BRIEF DESCRIPTION OF THE DRAWING FIGURES

DETAILED DESCRIPTIONS OF THE PREFERRED EMBODIMENTS

Figure 1:
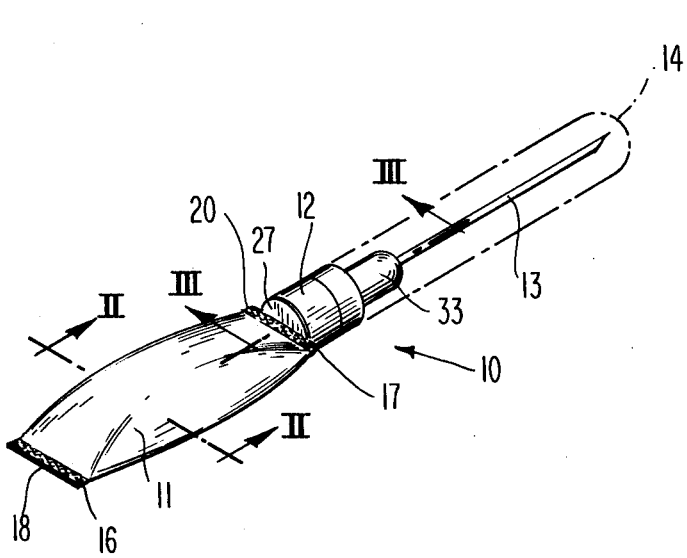
FIG. 1 is a perspective view of a disposable dispensing syringe in accordance with the present invention with a removable cap therefor being illustrated in phantom.

Referring now to the drawings in detail, reference is first made to FIG. 1, wherein there is illustrated a disposable syringe in accordance with this invention, generally designated by numeral 10. The syringe 10 includes a flexible-walled collapsible tubular container 11, a needle carrier 12, a needle 13 carried thereby, and a removable protective cover illustrated in phantom, and identified by the numeral 14.

Figure 2:
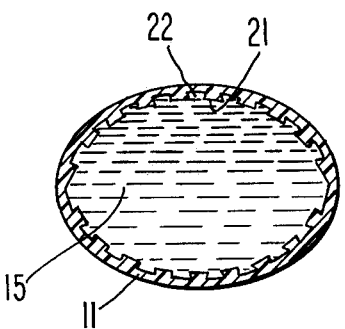
FIG. 2 is an enlarged cross-sectional view taken through the container portion of the device of FIG. 1, generally along the line II—II of FIG. 1, illustrating a medicine or the like contained therein.

A medicine, serum or the like 15 is provided inside the tubular container 11, as illustrated in FIG. 2. The liquid or other dispensable product 15 is normally present in the container 11, in a slight vacuum, or negative pressure, and is sealed therein, against bacterial communication from outside the container 11.

In a preferred form, the container 11, is constructed as an elongated extruded tube, that is provided with seals (for example, heat seals 16 and 17 at opposite ends 18 and 20, respectively). The material of construction of the container 11 will be a suitable plastic or the like that is inert to medicines to be contained therein.

Figure 5:
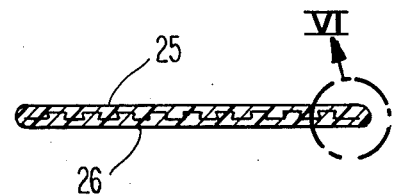
FIG. 5 is an enlarged transverse sectional view taken through the container portion of the device illustrated in FIG. 4, generally along the line V—V of FIG. 4.
Figure 4:
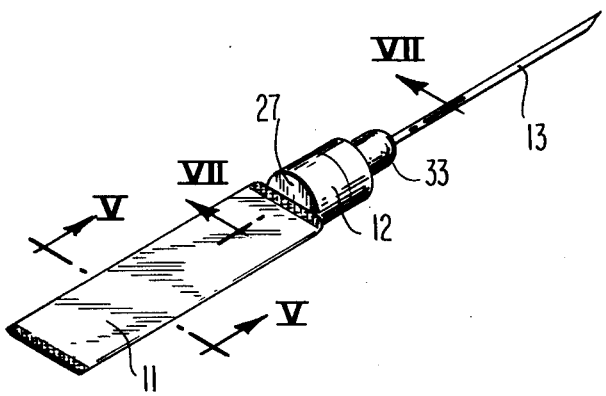
FIG. 4 is a perspective view of the device of this invention, generally like that of FIG. 1, but wherein the tubular container is illustrated in its flattened condition.
Figure 6:
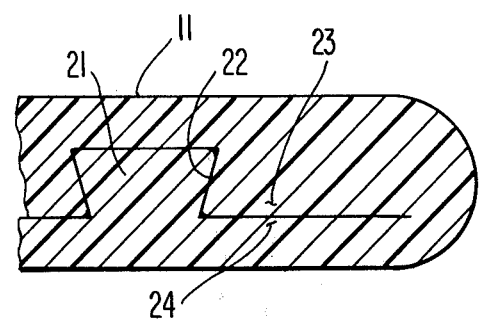
FIG. 6 is an enlarged detail view of one edge of the collapsed container of FIG. 5, the detail being that indicated as VI in FIG. 5, and illustrating with greater clarity the manner in which the mutual interengagement of opposed wall portions of the flattened container is complete even to the edge of the container illustrated in the detail.

The interior wall of the container 11 is provided with a plurality of longitudinally directed protrusions 21 alternately adjacent recesses 22, and such protrusions 21 and recesses 22 in the aggregate provides a tongue-and-groove arrangement encompassing the entire interior surface of the container 11, as is illustrated at FIG. 2, for facilitating complete surface-tp-surface interconnection between opposed interior wall portions upon flattening the container 11 as illustrated in FIGS. 4 and 5, for example. It will be noted, with particular reference to FIGS. 2, 5 and 6, that the tongue-in-groove arrangement extends as close as possible to the edge 22 of the container 11, to prevent opposed wall portions 23 and 24 from leaving a gap therebetween that could potentially contain undispensed medicant when the rest of the container 11 was flattened, if the interconnecting means provided by the tongue-in-groove arrangement did not go as close as possible to the flattened edges 22, as illustrated in FIG. 6. It will be clear from the arrangement illustrated that the tongue-in-groove arrangement or other interconnecting means will preferably permit the type of flattening for the opposed wall portions near the edges 22 that is illustrated at FIG. 6.

It will further be apparent that the tongue-and-groove arrangement may take on other forms than those illustrated in FIGS. 2, 5, and 6. For example, the interconnecting means could have rounded configurations, rectangular configurations (as viewed in transverse, cross-section), or any of the arrangements that will accommodate interconnection, and as are disclosed for example in U.S. Pat. Nos. 3,260,412; 3,160,323; 3,198,392, or elsewhere. In fact, it will be apparent that suitable interconnecting means need not be of the alternate recess and protrusion type longitudinally arranged as illustrated at FIG. 2, but that such could be comprised of alternate recess and protrusion arrangements that extend transversely of the containers. In fact, even a multiplicity of single, generally round, button or snap type locking members could be provided on opposed interior surface portions of the container 11, all within the spirit and scope of the broader aspects of the present invention. However, it will be apparent, that when complete expression of the medicant or other substance from a container is desired, a sufficiently great number of such interconnecting means will be required as will effect a substantially complete surface-to-surface interengagement between opposed layers of a flattened carrier, so as to permit complete expression of the substance being dispensed therefrom. It will be apparent from the foregoing that when reference is made to "interconnecting means", a "locking" arrangement will be understood.

The closures 16 and 17 will preferably be of a heat seal type, as aforesaid, but could comprise any suitable adhesive as will accomplish the purposed of preventing bacterial introduction, and of sealing the liquid in the container 11.

Figure 3:
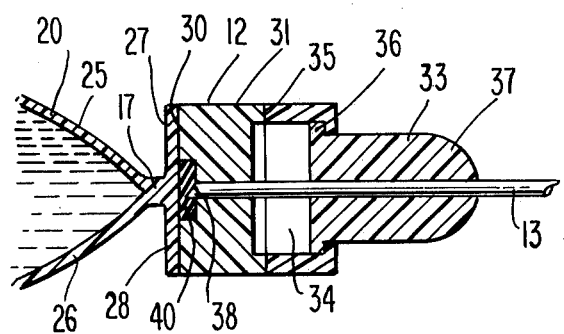
FIG. 3 is an enlarged fragmentary longitudinal sectional view, taken through the needle carrier portion of the device of this invention, illustrating the end of the container adjacent the needle carrier portion, the view being taken generally along the line III—III of FIG. 1.

With particular reference to the closure 17 at the dispensing end of the container 11, reference is made to FIG. 3, wherein it will be seen that the opposed wall portions 25 and 26 are merged together as one at 17, and that the closure portion 17 therefor comprises a thin seal extending linearly at the end 20 of the container 11, between the container 11 and the needle carrier 12, and that the closure portion 17 has no substantial thickness, other than the essential thickness of the tubes of the layers of material 25 and 26, joined together at that point. This is for facilitating complete expression from that portion of the container 11 that is closest to the dispensing mechanism 12, 13, in accordance with a principal purpose of the present invention.

For this purpose, in the manufacture of a container 11, opposed flaps 27 and 28 are provided, preferably as integral components of the wall portions 25 an 26 of the container 11, with the flaps 27 and 28 being directed away from each other, and to be separated 180° as will be apparent from FIG. 3, and to then be adhered by heat sealing, adhesive techniques or the like to the adjacent end 30 of the needle carrier member 12 such that the container closure portion 17 is disposed immediately adjacent the end 30 and in line with the adjacent end of a needle 13.

Figure 7:
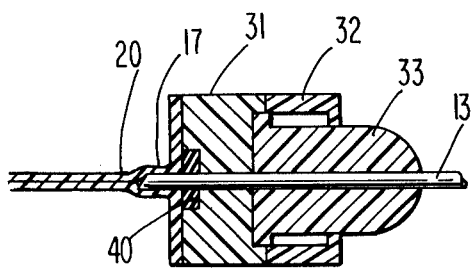
FIG. 7 is an enlarged fragmentary longitudinal sectional view of the needle carrier portion and adjacent end of the container, taken generally along the line VII—VII of FIG. 4, and wherein the needle is illustrated in communicating position with the interior of the container, as opposed to the non-communicating view of the needle as illustrated in FIG. 3.

The carrier member 12, in a preferred construction, may comprise a first part 31 and a second part 32, that has been independently manufactured and secured together along a parting line 35 by adhesive, heat sealing techniques, or in any suitable way. One or both of the parts 31 and 32 are provided with a cavity 34 therein that provides a plunger guideway for accomodating a plunger 33. The plunger 33 has a peripheral guide portion 36 and an axially protruding needle gripping portion 37. It will be seen with reference to FIGS. 3 and 7, respectively, that the plunger 33 is moveable between the two positions illustrated depending upon the desired position of the needle 13; i.e., non-communicating with the interior of the container 11, or in communicating relation therewith. Thus, the plunger 33 is secured to the needle 13, so that both the plunger 33 and the needle 13 moves together. It will be noted that the left end of the needle 13 is provided with a piercing means 38, or pointed portion, for breaking through the adjacent end portion 17 of the bag 11, and also preferably through a neoprene or rubber or other suitably constructed seal 40 between the member 12 and closure portion 17, as is illustrated in FIGS. 3 and 7. In some instances, the seal 40 may be dispensed with, but in most instances, it will be preferred as an additional means for sealing off the end 20 of the container 11, especially if the closure portion 17 is not in heat sealed condition. It will therefore be seen, that the needle 13 will normally be carried in the approximate position illustrated in FIG. 3, during shipment and the like, but that, when dispensing is desired, the plunger 33 will be grasped and moved rearwardly, or leftwardly as viewed in FIGS. 3 and 7, such that the leftmost end of the needle 13 will pierce the seal 40, the closure portion 17, and communicate into the interior of the container 11, for facilitating the dispensing of the contents therefrom.

It will further be apparent that the needle 13 may take on various forms, as being a long needle, a short needle, may comprise a perforated tube for a desired "spray" distribution in some instances, both medically related and non-medically related. Also, the relative dimensions illustrated in the drawings are not critical in that what has been referred to herein as a "needle" may in some instances be no substantially greater thickness than is conventionally understood for an inoculating type needle. For example, for use as a delivery tube for a contraceptive jelly, or other suitable passageway, the needle 13 may be substantially thicker than it would appear in the drawing illustrations. Also the needle 13 or other suitable passageways may be short and blunt, or substantially elongated for difficult-to-reach applications. For example, for use as a nasal applicator, a longer, thicker tube may be desired.

It will also be apparent that in accordance with the device of the present invention, certain non-medically related uses may embody the essence of the present invention, and it is intended that such fall within the scope of the invention as defined in the appended claims.

Even further, it will be understood that various other constructions may be used to embody the concept of the present invention, within the spirit and scope of the claims and as is elsewhere recited as being objectives of the present invention. Furthermore, various other features may be employed in connection with the present invention, for example those disclosed in my earilier above-mentioned U.S. Pat. No. 3,192,925 the disclosure of which is herein incorporated by reference.

It will be apparent from the foregoing that the various objectives of the present invention will be fulfilled.

What is claimed is:

1. A disposable syringe comprising a collapsible container for containing medicine or the like therein, needle carrier means secured to the container at a discharge end thereof, means closing the container at said end, said needle carrier means including needle means normally being disposed out of communication with the interior of said container but being movably disposed for communicating with the interior of said container for dispensing medicine or the like therefrom, said container being of sufficiently flexible construction to facilitate flattening thereof upon dispensing from the container, said discharge end of said container, at its location of securement to said needle carrier means being free of any non-flattenable zone that would inhibit complete discharge from the container at that end, inhibit complete said discharge end of said container including flaps outwardly of said container end closure, said flaps being in secured engagement with an adjacent end of said needle carrier means outwardly of said end closure.

2. The syringe of claim 1, wherein said end closure comprises heat seal means.

* * * * *